United States Patent [19]

Kunishima et al.

[11] Patent Number: 4,495,348
[45] Date of Patent: Jan. 22, 1985

[54] DERIVATIVE OF CEPHAMYCIN C

[75] Inventors: Mamoru Kunishima, Saitama; Masahiko Yabuuchi, Yono; Minoru Masuda; Kikuo Imazumi, both of Ageo; Hiroaki Hamano, Higashimurayama, all of Japan

[73] Assignee: Nippon Kayaku Kabushiki Kaisha, Tokyo, Japan

[21] Appl. No.: 324,475

[22] Filed: Nov. 24, 1981

[30] Foreign Application Priority Data

Dec. 4, 1980 [JP] Japan .................. 55-170274

[51] Int. Cl.$^3$ ................ C07D 501/57; A61K 31/545
[52] U.S. Cl. ..................... 544/021; 544/016
[58] Field of Search ............... 544/16, 28, 21, 30; 424/246

[56] References Cited

U.S. PATENT DOCUMENTS

| | | | |
|---|---|---|---|
| 3,725,400 | 4/1973 | Voser | 260/243 C |
| 4,053,286 | 10/1977 | Weinstock | 544/21 |
| 4,168,375 | 9/1979 | Andrisano et al. | 544/20 |
| 4,173,702 | 11/1979 | Gorman et al. | 544/21 |
| 4,283,492 | 8/1981 | Imanaka et al. | 435/47 |
| 4,302,578 | 11/1981 | Stapley et al. | 542/427 |

FOREIGN PATENT DOCUMENTS

| | | |
|---|---|---|
| 54-141794 | 11/1979 | Japan . |
| 185293 | 5/1981 | Japan . |
| 463286 | 8/1981 | Japan . |
| 4950593 | 11/1981 | Japan . |
| 143800 | 6/1976 | United Kingdom . |

OTHER PUBLICATIONS

McElvain, The Characterization of Organic Compounds, p. 174, (1953).

Primary Examiner—Nicholas S. Rizzo
Attorney, Agent, or Firm—Wegner & Bretschneider

[57] ABSTRACT

Disclosed are an N-benzenesulfonyl derivative of cephamycin C represented by the following formula:

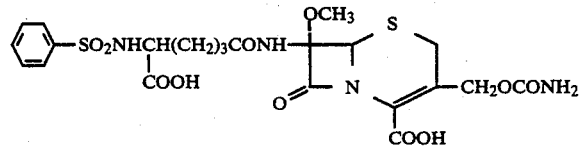

which can easily be separated as a solid from an aqueous solution thereof, and a process for the preparation thereof.

This derivative is valuable as an intermediate leading to a cephamycin type antibiotic substance.

1 Claim, No Drawings

DERIVATIVE OF CEPHAMYCIN C

BACKGROUND OF THE INVENTION

Cephamycin C is an important substance as a starting compound for the production of a cephamycin type antibiotic substance. However, since the water solubility of this compound is very high, it is very difficult to purify and isolate this compound. Accordingly, various studies have been made for developing methods for purifying and isolating cephamycin C, and some methods are known. For example, there can be mentioned an adsorption-elution method using active carbon. However, this method involves various problems encountered when this method is carried out on an industrial scale and hence, this method is not preferred from the commercial viewpoint. There also is known a method for purification and isolation of cephalosporin C, cephamycin A and cephamycin B in which extraction and purification are performed by adsorption and desorption using a macroporous non-ionic adsorbent resin (see U.S. Pat. No. 3,725,400 and Japanese Patent Application Laid-Open Specification No. 3286/71). According to experiments made by us, it has been found that cephamycin C cannot be adsorbed on such resin.

Furthermore, there is known a method in which cephamycin C contained in a fermentation liquid is converted to a derivative soluble to some extent in an organic solvent and the derivative is extracted with an organic solvent (see Japanese Patent Application Laid-Open Specification No. 50593/74). However, in this method where the intended compound is extracted from a large quantity of a dilute aqueous solution with an organic solvent, a relatively large amount of the organic solvent is consumed, and impurities having physicochemical properties similar to those of cephamycin C are modified and converted to derivatives similar to the cephamycin C derivative and they are extracted together with the cephamycin C derivative, with the result that the purity of the obtained product is likely to be reduced. Therefore, this method is not satisfactory.

Under such background, we previously proposed a process in which cephamycin C is converted to an acyl derivative and the derivative is isolated by using a macroporous non-ionic adsorbent resin (see Japanese Patent Application Laid-Open Specification No. 141794/79).

SUMMARY OF THE INVENTION

The present invention relates to a novel derivative of cephamycin C and a process for the preparation thereof. More particularly, the present invention relates to an N-benzenesulfonyl derivative of cephamycin C represented by the following formula (I):

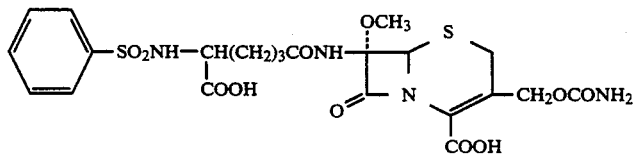

and a process for the preparation of an N-benzenesulfonyl derivative of cephamycin C, which comprises reacting cephamycin C in an aqueous solution with benzenesulfonyl chloride to obtain an aqueous solution of an N-benzenesulfonyl derivative of cephamycin C represented by the above formula (I), precipitating the N-benzenesulfonyl derivative of cephamycin C from the solution and recovering said derivative. It is a primary object of the present invention to convert cephamycin C in an aqueous solution to a derivative precipitating easily in water and isolate and collect cephamycin C in the form of said derivative in a high yield from the aqueous solution.

The compound of the present invention is novel and is important as a starting substance for production of various valuable cephalosporin derivatives.

DETAILED DESCRIPTION OF THE INVENTION

Any of cephamycin C containing culture filtrates and other aqueous solutions containing cephamycin C may be used as the starting aqueous solution of crude cephamycin C in the present invention. However, in the present invention, there are preferably used a resin-treated liquid obtained by passing a cephamycin C containing culture filtrate through a non-ionic adsorbent resin such as Diaion HP 20 ® and a resin eluate obtained by passing a cephamycin C containing culture filtrate through an ion-exchange resin such as Amberlite IRA-411 ® to make cephamycin C adsorbed in the resin and eluting the adsorbed cephamycin C in water which may contain an organic or inorganic salt such as sodium acetate, sodium sulfate or sodium chloride.

In production of the N-benzenesulfonyl derivative of cephamycin C according to the present invention, an inorganic base such as sodium hydroxide or sodium carbonate is added to an aqueous solution containing cephamycin C to adjust the pH value at 8 to 10.5, benzenesulfonyl chloride is gradually added in an amount of 1 to 5 equivalents to cephamycin C to the aqueous solution with stirring, and reaction is then carried out preferably at a temperature of 15° to 20° C. and a pH value of 8 to 10.5. After completion of the reaction, the pH value is lowered to 5 to 7 again and insoluble substances are removed. The obtained aqueous solution is concentrated under reduced pressure until the volume is reduced from ½ to 1/30. When the pH value of the concentrate is adjusted to 1 to 3, preferably 2.0 to 2.5, by an acid, the intended N-benzenesulfonyl derivative of cephamycin C is precipitated.

The precipitate is collected, washed with water and dried in vacuo, whereby the N-benzenesulfonyl derivative (I) of cephamycin C is obtained in the form of a powder of a free acid.

When the intended compound is isolated from a solution containing relatively large quantities of impurities, for example, a solution obtained by reacting benzenesulfonyl chloride with a resin-treated liquid formed by passing a cephamycin C containing culture filtrate through a non-ionic adsorbent resin or a mother liquor left after collection of a precipitate of the cephamycin C derivative (I), it is preferred that the impurities be removed in advance. For example, there may be adopted a method in which a solution containing the cephamycin C derivative (I) and impurities is passed through a non-ionic adsorbent resin such as Diaion HP-20 ® or AF Resin ® to make the cephamycin C derivative (I) adsorbed on the resin and then the cephamycin C derivative (I) is eluted with water which may contain a hydrophilic organic solvent such as alcohol or acetone.

When the so obtained free acid powder is dissolved in an alcohol such as methanol or ethanol or acetone and an alkali metal salt such as potassium hydrogencarbonate or an organic base such as triethylenediamine is added in an amount of 0.5 to 1.0 equivalent to the solution with stirring, a salt of the cephamycin C derivative (I) is obtained as a precipitate. By conducting this step, impurities can be further removed.

The compound of the present invention can easily be precipitated in the solid form even without converting it to a salt in the foregoing manner, and the compound of the present invention can be purified and isolated in a high yield without passing through the extraction step. Accordingly, the compound of the present invention is very valuable from the industrial viewpoint.

The present invention will now be described in detail with reference to the following Examples.

EXAMPLE 1

(A) 40 l of a cephamycin C containing culture filtrate

Stirring was then conducted for 30 minutes under cooling to 5° C., and the formed precipitate was recovered by filtration.

The precipitate was washed with water and dried in vacuo to obtain 43.3 g of N-benzenesulfonylcephamycin C.

By the high speed liquid chromatography, it was confirmed that the purity was 88.9%, and the yield was 73.3%.

(B) In order to obtain a product having a higher purity, 4.0 g of the so obtained powder was dissolved in 30 ml of ethanol, and the solution was passed through a column packed with 250 ml of Sephadex LH-20 ® and 100 ml of a fraction of N-benzenesulfonylcephamycin C was recovered and concentrated under reduced pressure. Then, the concentrate was dissolved in a small amount of acetone and petroleum ether was added to the solution to effect precipitation and obtain 2.1 g of a white powder.

The purity determined by the high speed liquid chromatography was 96.8%, and the melting point was 162° C. (decomposition).

Specific rotatory power: $[\alpha]_D^{20} + 114.4°$ (C=1.01, methanol).

Ultraviolet absorption spectrum: $\lambda_{max}^{methanol}$ 222 nm ($E_1\,_{cm}^{1\%}$ 216).

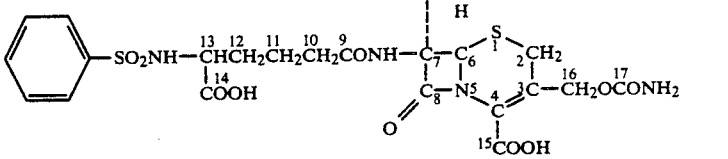

(containing 241 g of cephamycin C) was passed through a column packed with 12 l of an anion-exchange resin (Amberlite IRA-411 ®, acetic acid type) to make cephamycin C adsorbed in the resin. The resin was washed with water and elution was carried out by using a 0.2N acetic acid buffer solution having a pH value of 5.5 to recover 36 l of a cephamycin C containing eluate (containing 202 g of cephamycin C). The recovered eluate was concentrated under reduced pressure to obtain 10 l of a resin eluate (containing 199 g of cephamycin C).

A 6N aqueous solution of sodium hydroxide was added to 2.0 l of the resin eluate (containing 39.8 g of cephamycin C) to adjust the pH value of 9.0, and 31.6 g (2 equivalents) of benzenesulfonyl chloride was added to the resin eluate with stirring while maintaining the reaction temperature at 15° to 20° C.

After completion of the addition, the reaction mixture was stirred to effect reaction. During the reaction, a 6N aqueous solution of sodium hydroxide was appropriately added to maintain the pH value at 8.0 to 9.0.

After completion of the reaction, 6N hydrochloric acid was added to the reaction mixture with stirring to adjust the pH value to 5.5. The formed insoluble substances were removed by filtration to obtain 2.2 l of a solution containing 47.3 g of N-benzenesulfonylcephamycin C.

The solution was concentrated under reduced pressure so that the volume was reduced to 500 ml, and the concentrate was cooled to 5° C. and concentrated hydrochloric acid was added to the concentrate with stirring. The pH value was adjusted to 2.0 to form a precipitate.

The $^{13}$C-NMR spectrum ($\delta$) of the above substance in heavy acetone was as follows: 22.1 (C-11), 26.9 (C-12), 33.3 (C-2), 35.6 (C-10), 53.4 (—OCH$_3$), 56.5 (C-6, C-H), 63.5 (C-16), 64.8 (C-13, C-H), 96.9 (C-7), 125.0 (C-3), 127.9 (aromatic), 129.9 (aromatic), 133.3 (aromatic), 142.3 (aromatic), 129.2 (C-4), 157.7 (C-9), 161.6 (C-14), 163.0 (C-8), 173.0 (C-15), 174.0 (C-17)

The infrared absorption spectrum (KBr tablet method) of this compound had characteristic absorptions at 1770 cm$^{-1}$, 1725 cm$^{-1}$, 1690 cm$^{-1}$ and 1330 cm$^{-1}$.

EXAMPLE 2

The pH value of the mother liquor (810 ml) left after recovery of 43.3 g of N-benzenesulfonylcephamycin C in Example 1 was adjusted to 3.0 by a 6N aqueous solution of sodium hydroxide, and the mother liquor was passed through a column packed with 400 ml of Diaion HP-20 ® to make N-benzenesulfonylcephamycin C adsorbed in the resin. The resin was washed with water and elution was carried out with a 0.04N aqueous solution of sodium acetate to obtain 1300 ml of an eluate containing 3.5 g of N-benzenesulfonylcephamycin C. The eluate was concentrated under reduced pressure so that the volume was reduced to 30 ml. Concentrated hydrochloric acid was added to the concentrate with stirring under cooling to 5° C. to adjust the pH value of 2.0 and effect precipitation. Stirring was further conducted under cooling to 5° C. for 20 minutes, and the formed precipitate was recovered by filtration. The recovered precipitate was washed with water and dried in vacuo to obtain 3.7 g of N-benzenesulfonylcephamycin C. The purity determined according to the high speed liquid chromatography was 85.0%, and the yield was 76.5%.

EXAMPLE 3

The pH value of 4500 ml of a cephamycin C containing culture filtrate (containing 30.2 g of cephamycin C) was adjusted to 5.0 by acetic acid, and the filtrate was passed through a column packed with 900 ml of a non-ionic adsorbent resin (Diaion HP-20 ®) to obtain 5900 ml of a resin-treated liquid. The pH value of the resin-treated liquid was adjusted to 9.0 by addition of a 6N aqueous solution of sodium hydroxide, and 59.9 g (5 equivalents) of benzenesulfonyl chloride was added to the resin-treated liquid with stirring. After completion of the addition, reaction was carried out for 2 hours with stirring. During the reaction, the pH value was maintained at 8.0 to 9.0 by appropriately adding a 6N aqueous solution of sodium hydroxide. The reaction temperature was maintained at 15° to 20° C.

After completion of the reaction, 6N hydrochloric acid was added to the reaction mixture to adjust the pH value to 5.5, and the formed precipitate was removed by filtration to obtain 5150 ml of a solution containing 31.8 g of N-benzenesulfonylcephamycin C.

The pH value of 750 ml of the so obtained solution (containing 4.6 g of N-benzenesulfonylcephamycin C) was adjusted to 3.0 by 6N hydrochloric acid and the solution was passed through a column packed with 200 ml of a non-ionic adsorbent resin (AF Resin ®) to make the intended substance adsorbed in the resin. The resin was washed with water and elution was carried out with a 0.4N aqueous solution of sodium acetate containing 50% of acetone to obtain 645 ml of an eluate containing 4.1 g of N-benzenesulfonylcephamycin C.

The eluate was concentrated under reduced pressure so that the volume was reduced to 35 ml, and the concentrate was cooled to 5° C. and concentrated hydrochloric acid was added with stirring to adjust the pH value to 2.0 and cause precipitation.

Stirring was further conducted for 20 minutes under cooling to 5° C., and the formed precipitate was recovered by filtration, washed with water and dried in vacuo to obtain 3.9 g of N-benzenesulfonylcephamycin C.

The purity determined according to the high speed liquid chromatography was 85.9%, and the yield was 71.7%.

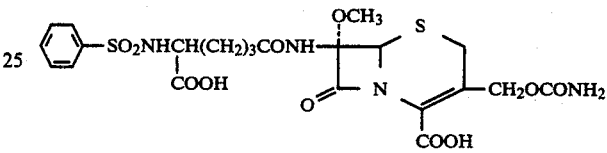

What is claimed is:

1. An N-benzenesulfonyl derivative of cephamycin C represented by the following formula: